US012644887B2

(12) United States Patent
Shen et al.

(10) Patent No.: US 12,644,887 B2
(45) Date of Patent: Jun. 2, 2026

(54) TEST STRIP FOR DETECTING ANALYTE IN SAMPLE

(71) Applicant: Zhejiang Orient Gene Biotech Co., Ltd, Huzhou (CN)

(72) Inventors: Lili Shen, Huzhou (CN); Fangli Zhou, Huzhou (CN); Shenping Zhu, Huzhou (CN); Zhaoxia Yao, Huzhou (CN); Yu Peng, Huzhou (CN)

(73) Assignee: Zhejiang Orient Gene Biotech Co., Ltd, Huzhou (CN)

( * ) Notice: Subject to any disclaimer, the term of this patent is extended or adjusted under 35 U.S.C. 154(b) by 974 days.

(21) Appl. No.: 17/865,162

(22) Filed: Jul. 14, 2022

(65) Prior Publication Data

US 2023/0084255 A1 Mar. 16, 2023

(30) Foreign Application Priority Data

Sep. 15, 2021 (CN) .......................... 202111083079.5
Sep. 15, 2021 (CN) .......................... 202122236352.5

(51) Int. Cl.
*G01N 33/543* (2006.01)
(52) U.S. Cl.
CPC .............................. *G01N 33/54388* (2021.08)
(58) Field of Classification Search
CPC ..................................... G01N 33/54388–54389
See application file for complete search history.

(56) References Cited

U.S. PATENT DOCUMENTS

| | | | |
|---|---|---|---|
| 4,976,923 A | 12/1990 | Lipsky et al. | |
| 5,429,804 A | 7/1995 | Sayles | |
| 6,194,225 B1 * | 2/2001 | Oka ................. | G01N 33/54388 |
| | | | 436/514 |
| 6,534,324 B1 * | 3/2003 | Zin .................. | G01N 33/54388 |
| | | | 436/514 |
| 6,726,879 B2 | 4/2004 | Ng et al. | |
| 2003/0027359 A1 | 2/2003 | Hudak et al. | |
| 2012/0308444 A1 * | 12/2012 | Zhu ......................... | B82Y 15/00 |
| | | | 156/306.6 |
| 2013/0244314 A1 * | 9/2013 | Yuki ................. | G01N 33/54388 |
| | | | 156/278 |
| 2014/0178976 A1 * | 6/2014 | Baydoun ............ | G01N 33/5302 |
| | | | 422/421 |
| 2020/0200747 A1 * | 6/2020 | Chand ................ | G01N 21/6428 |

* cited by examiner

*Primary Examiner* — Maris R Kessel
*Assistant Examiner* — Alea N. Martin
(74) *Attorney, Agent, or Firm* — MUNCY, GEISSLER, OLDS & LOWE, P.C.

(57) ABSTRACT

A test strip main body with a sample section, colloidal gold pads, an NC film and a water absorption end in sequence; and the colloidal gold pads are of 3 to 8 layers. Compared with the prior art, the test strip has higher sensitivity, which is beneficial to detection of trace or low-concentration samples.

13 Claims, 3 Drawing Sheets

TEST STRIP FOR DETECTING ANALYTE IN SAMPLE

CROSS REFENCE OF THE RELATED APPLICATION

The present application claims the benefit of Chinese Patent Application No. 202122236352.5, filed on 15 Sep., 2021, and, 202111083079.5, filed on 15 Sep., 2021. The content of these applications including all tables, diagrams and claims is incorporated hereby as reference it its entirety.

TECHNICAL FIELD

The present invention relates to the technical field of colloidal gold immunochromatography, in particular to a test strip including colloidal gold pads.

BACKGROUND

The following background art is provided to assist the reader in understanding the present invention and cannot be regarded as prior art.

Illegal drug abuse has become a recognized and worsening social problem in our society. In 2003, the United States Department of Health and Human Services found by investigation that approximately 19.5 million Americans, or 8.2% of the population over the age of 12, were taking illegal drugs. "Recently-used illegal drugs" refers to an illegal drug having used within one month prior to investigation of the United States Department of Health and Human Services. Hemp was found to be the most commonly used illegal drug, accounting for 6.2% (14.6 million). An estimated 2.3 million people (1.0%) are now using cocaine, 604,000 people are using crack, 1 0 million people are using hallucinogens, and an estimated 119,000 people are using heroin. With the development of the times, many new drugs are constantly emerging, which is called one of the important social problems currently in the world.

To combat drug abuse and monitor this social problem, drug test has become standard test procedures in industries such as employment, education, sports, law enforcement, etc. To promote this effort, a drug test industry has formed. This industry offers a wide variety of drug test products. A urine sample collection cup for sample analysis is a classic test product. These devices may be complicated, difficult or dirty for users, or may cause problems of sample adulteration to conceal the situation of recent use of illegal drugs. Additionally, urine samples can not be collected in certain occasions, such as on the roadside or in public.

Using detection devices to collect liquid samples, such as urine, and determining the presence or absence of specific analytes (such as drugs and/or their metabolites, or markers associated with diseases) have become very common methods. Such testing devices generally require that a sample is collected in a sample container, the relevant technician inserts a test strip and submerges a portion of the test strip in the sample, and then removes the test strip to read a result. The technician may contact with the sample, and his health may be endangered or the sample may be contaminated. To avoid this risk, it is necessary to operate after the sample collection container is covered with a closing lid. Currently, there have been many closing devices, such as devices disclosed in U.S. Pat. Nos. 4,976,923, 5,429,804, and 6,726, 879. For these devices, a test strip is fixed on a cover of a test device. When in use, a container is turned over or tilted so that a sample soaks the test strip for detection. US patent application US2003/0027359A1 published on Feb. 6, 2003 discloses a urine detection cup. For the urine detection cup, after a cover covers an opening of the cup, a push rod still needs to push a column-type piston to move, so that a fluid sample flows out of a cup cavity and wets a detection element. Chinese published patent application 200510113977.5 discloses a urine detection cup. For the urine detection cup, the start of detection is initiated by initiating the flow of a liquid from a collection cavity to a detection cavity after a cover covers an opening of the cup. Another Chinese published patent application 200480033286.8 also discloses a urine detection cup. For the urine detection cup, the start of detection is initiated after a cover covers an opening of the cup.

Many other sample collection and test devices are inefficient in extracting samples from collection devices, and there are always many problems, such as contaminating the environment by sample leakage, or affecting detection results by collecting too few or too much samples, or many operation steps to make detection complicate. Many of these devices are also very complex in their design and manufacture and require the use of relatively expensive materials. Therefore, there is a need for better methods and devices for sample collection and detection.

Recently, such detection devices have been increasingly adopted by ordinary households or non-professional institutions. Since these detection evaluations are designed for non-professionals, these detection devices need to be simple to operate and to ensure the accuracy of detection results. Therefore, a detection device with simple operation and accurate and reliable detection results is required by the current society. The present invention provides a detection device that meets this requirement.

At present, test strips or detection cards, etc. developed by using colloidal gold immunochromatography technology are widely used in medicine or in ordinary people's homes. These test strips or detection cards are simple and fast, and ordinary people can use them to obtain detection results in one minute or at most ten minutes, such as colloidal gold test strips for early pregnancy detection. Therefore, it is of great significance to further improve these test strips or detection cards.

Existing colloidal gold test strips generally consist of a sample pad, a colloidal gold pad, an NC film, a water absorption material, etc. Among them, the colloidal gold pad is mostly of one layer, and the test strips composed thereof are often not sensitive enough to meet detection of trace or low-concentration samples.

This requires the further improvement of the existing test strips to meet different test needs and make test results more accurate.

SUMMARY

The purpose of the present invention is to provide a colloidal gold test strip with higher sensitivity.

The purpose of the present invention is achieved through the following technical solutions.

A test strip includes a test strip main body. The test strip main body is provided with a sample section, colloidal gold pads, an NC film and a water absorption end in sequence; and the colloidal gold pads are of 3 to 8 layers.

Further, the colloidal gold pads include colored parts and white edge parts.

The colloidal gold pads are generally made of colloidal gold coated on non-woven fabric or glass fiber. The colloidal gold is an aqueous solution of chloroauric acid, has high electron density, can bind to a variety of biological macro-molecules, and is a non-radioactive tracer commonly used in immunolabeling technology.

Preferably, a length of the white edge parts is 2 to 8 mm.

Preferably, the colloidal gold pads are overlapped in a straight line; and the white edge part of one of the colloidal gold pads is overlapped on an upper side of the colored part of another adjacent colloidal gold pad.

Further, an overlapping length of the white edge part of one of the colloidal gold pads and the colored part of another colloidal gold pad is not more than 6 mm.

Further, after the white edge part of one of the colloidal gold pads overlaps with the colored part of another colloidal gold pad, the colored part thereof can further overlap with the colored part of another colloidal gold pad, and an overlapping length of the colored part thereof and the colored part of another colloidal gold pad is not more than 6 mm.

Preferably, an overlapping length of the colored part of one of the colloidal gold pads and the colored part of another colloidal gold pad is not more than 5 mm.

Preferably, the test strip includes a strap, which can cover all the colloidal gold pads to protect the colloidal gold pads and make the colloidal gold pads bind more tightly.

Further, the strap includes an adhesive sticker section and a sample section; the adhesive sticker section is used for bonding the strap to other components to play a fixing role; and the sample section can be made of non-woven fabric, glass fiber and other materials, and is an addition part for samples.

Preferably, the strap is provided with strips, so that the colloidal gold pads can be overlapped more tightly; the number of the strips is greater than or equal to 2; and PVC strips or PS strips can be used as the strips.

On the other hand, the present invention provides a test strip for detecting an analyte in a sample, including a test strip main body, wherein the test strip main body is sequentially provided with a sample pad, a labeling pad, an NC film with a detection area, and a water absorption area pad; and the labeling pad includes a plurality of labeling pad bodies overlapped end to end with each other.

In some manners, labeling substances on the labeling pad bodies are the same labeling substance.

In some manners, the labeling substances in a labeling area include antibodies specifically binding to the analyte in the sample and colored particles coupled with the antibodies.

In some manners, the labeling pad bodies include colored areas sprayed with the labeling substances and white areas not containing the labeling substances.

In some manners, a length of the white areas is 2 to 8 mm.

In some manners, a length of the colored areas is 2 to 8 mm.

In some manners, the plurality of labeling pad bodies are overlapped end to end in a straight line; and a white area part of one of a plurality of colloidal gold pads is overlapped on an upper side of a colored part of another adjacent colloidal gold pad.

In some manners, an overlapping length of a white part of one of the plurality of labeling pad bodies and a colored part of another one of the plurality of labeling pad bodies is not more than 6 mm.

In some manners, an overlapping length of the white part of one of the plurality of labeling pad bodies and the colored part of another one of the plurality of labeling pad bodies is not more than 5 mm.

In some manners, an overlapping length of a white part of one of the plurality of labeling pad bodies and a colored part of another one of the plurality of labeling pad bodies is not more than 4 mm.

In some manners, the labeling pad bodies include 3 to 8 labeling pad bodies.

In some manners, the labeling pad bodies are arranged in sequence from upstream to downstream.

In some manners, the labeling substances include gold particles or latex particles.

In some manners, the antibodies on the labeling pad bodies are antibodies specifically binding to THC, and the detection area on the NC film includes THC antigen substances. In some manners, the labeling pad bodies are 4 labeling pad bodies overlapped end to end.

In some manners, the antibodies on the labeling pad bodies are first antibodies specifically binding to HCG, and the detection area on the NC film includes second antibodies specifically binding to the HCG. In some manners, the labeling pad bodies are 5 labeling pad bodies overlapped end to end.

In some manners, the labeling pad bodies are 4 labeling pad bodies overlapped end to end.

In some manners, one end of the strap covers the sample pad, and the other end thereof is connected to NC.

In some manners, a material of the sample pad is non-woven fabric or glass fiber.

In some manners, the strap is provided with strips, so that the labeling pad bodies can be overlapped tightly; the number of the strips is greater than or equal to 2; and the strips include PVC strips or PS strips.

The advantages of the present invention are as follows: the present invention provides a test strip, and compared with the prior art, the test strip has higher sensitivity, which is beneficial to detection of trace or low-concentration samples.

BRIEF DESCRIPTION OF DRAWINGS

FIG. 3 is a color card.

Figure 1:
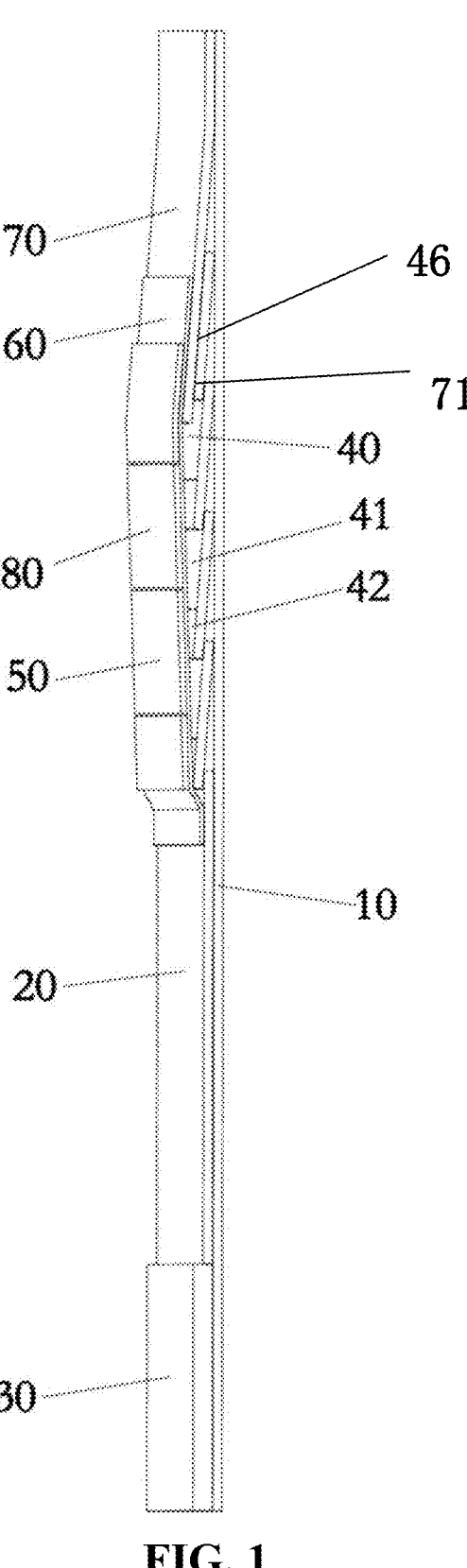
FIG. 1 is a structural schematic diagram of a test strip of the present invention.

In drawings: 10—test strip main body, 20—NC film, 30—water absorption end, 40—colloidal gold pad, 41—colored part overlapped by a sample pad, 42—white edge part, 50—strip, 60—adhesive sticker section, 70—sample section, 80—strap, 421—white area of a labeling pad overlapped on one end 201 of the NC film.

DETAILED DESCRIPTION

The structures involved in the present invention or the technical terms used are further described below. If there is no special indication, they should be understood and interpreted according to the general terms commonly used in the art.

Detection

Detection means assaying or testing for the presence or the absence of a substance or material such as, but not limited to, chemicals, organic compounds, inorganic compounds, metabolites, drugs or drug metabolites, organic tissue or metabolites thereof, nucleic acids, proteins or polymers. In addition, detection means testing the quantity of substances or materials. Further, assaying also means immunodetection, chemical detection, enzymatic detection, and the like.

Samples

Detection devices or collected samples of the present invention include biological fluids (e.g., case fluids or clinical samples). Liquid samples or fluid samples can be derived from solid or semi-solid samples, including excreta, biological tissue and food samples. The solid or semi-solid samples can be converted to a liquid samples by any suitable method, such as mixing, mashing, macerating, incubating, dissolving or using enzymolysis in a suitable solution (e.g., water, a phosphate solution or other buffer solutions) to digest solid samples. "Biological samples" include samples derived from animals, plants and food, such as urine, saliva, blood and components thereof, spinal fluid, vaginal secretions, sperms, feces, sweat, secretions, tissue, organs, tumors, tissue and organ cultures, cell cultures and media derived from human or animals A preferred biological sample is urine, preferably a biological sample is saliva. Food samples include food processing substances, final products, meat, cheese, wine, milk and drinking water. Plant samples include plant tissue, plant cell cultures and media derived from any plant. "Environmental samples" are derived from the environment (e.g., liquid samples derived from lakes or other water bodies, sewage samples, soil samples, groundwater, seawater, and waste liquid samples). The environmental samples may also include sewage or other waste water.

Any analyte can be detected by using a suitable detection element or test element of the present invention. Preferably, small drug molecules in the saliva and the urine are detected by using the present invention. Preferably, small molecular substances such as viruses and bacteria in the saliva, throat or nasal fluids can be detected. By using a collector 102 of the present invention, samples in any of the above forms, whether initially solid or liquid, can be collected, as long as these liquids or liquid samples can be absorbed by an absorbing element, which is generally located on the collector. The absorbing element 102 here is generally prepared from a water absorbing material, which is initially dry, and liquid samples or fluid samples can be absorbed through the capillary or other properties of the material of the absorbing element, so that the fluid samples are kept in the absorbing element. An absorbing material may be any material capable of absorbing liquids, such as sponge, filter paper, polyester fiber, gel, non-woven fabric, cotton, polyester films, yarn, flocking, and the like. When flocking swabs are used, flocking swabs described in the following patents may be used for collecting fluid samples as a part of the present invention: U.S. Pat. Nos. 8,114,027, 8,317,728, 8,979,784, 9,011,358, 9,173,779, 10,327,741, AU2004226798, JP4579902, ZL200610099310.9. In some manners, the absorbing element is rigid when dry, such as a sponge, which becomes soft when wet, and can be compressed after it becomes soft to release liquids. Of course, when it is a relatively sparse sponge, such as a sponge swab, which can also absorb liquid samples, and the absorbing amount of these liquid samples is very small, such as 5 to 100 microliters, for example, a sponge swab described in U.S. Provisional Application 63/300,811 applied on Jan. 19, 2022 is also a specific embodiment that can be used in the present invention as a collector.

Of course, the absorbing element is not necessarily prepared from a material with a water-absorbing property, it can be prepared from a non-water-absorbing material, but there are holes, threads, and caves on the absorbing element, and samples can be collected on these structures. These samples are generally solid or semi-solid samples, and are filled between threads, and in caves or holes to be collected. Of course, optionally, the absorbing element may be composed of some non-water-absorbing fibers and hair, and these materials are used for scraping solid, semi-solid or liquid samples to retain these samples on the absorbing element.

Downstream and Upstream

Downstream or upstream is divided for a liquid flow direction, generally a liquid or fluid flows from an upstream area to a downstream area. The downstream area receives a liquid from the upstream area, and the liquid can also flow along the upstream area to the downstream area. This is generally divided according to the liquid flow direction. For example, on some materials that use capillary force to promote liquid flow, the liquid can overcome gravity and flow in a direction opposite to the gravity. At this time, the upstream and downstream are still divided according to the liquid flow direction. For example, a test element mentioned in the present invention has a sample application area 10351, a labeling area 10352, a test area 20 and an absorption area 30. The sample application area is upstream of the labeling area, the test area is downstream of the labeling area, and the absorption area is downstream of the test area. Generally, a direction of a fluid flowing along the test element is from upstream to downstream.

Gas Communication or Liquid Communication

Gas communication or liquid communication means that a liquid or gas can flow from one place to another place, and may pass through some physical structures to play a role in guiding in a flowing process. Said passing through physical structures generally refers to that the liquid passes through the surfaces of these physical structures, or the internal spaces of these structures to passively or actively flow to another place. Passively generally means the flow caused by external force, such as the flow under capillary action, air pressure action, etc. The flow here may also refer to that the liquid or gas may also passively flow due to its own action (gravity or pressure), a fluid under the action of air pressure may flow in a forward direction, or it may flow in an opposite direction, or the fluid may also be promoted to flow from one location to another location under the action of air pressure. The communication here does not necessarily mean the presence of the liquid or gas, but only indicates the connection relationship or state between two objects in some cases. If there is a liquid, it can flow from one object to another object. This refers to the state in which the two objects are connected. On the contrary, if there is no liquid communication or gas communication state between the two objects, and if there is a liquid in or on one object, the liquid cannot flow into or onto the other object, such a state is a non-communication state, and a non-liquid or gas communication state.

Detachable Combination

A detachable combination means that the connection relationship between two components is in several different states or positional relationships. For example, when they are two physical components, they can be separated at first, and when in a suitable first case, they are connected or combined, and when in a suitable second case, the two components may be separated, this separation being physical separation in space without contact. Alternatively, the two components are combined at first, and when in a suitable case, the two components may be physically separated in space. Yet alternatively, two objects are separated at first, they are combined when needed to complete certain function, and then separated, or they are combined again later for certain purpose. In a word, the combination of the two or the separation between the two may be easily performed, and the combination or separation may be repeated for multiple cycles, of course, it may also be a one-time combination and separation. In addition, it may be a detachable combination of two components, or a pairwise detachable combination of three or more components. For example, there are first, second and third components, the first component and the second component are in a detachable combination, the second component and the third component may also be a detachable combination, and the first component and the third component may also be in a detachable combination or separation. In addition, a combination mode may be that the two objects are detachable themselves, or they may be indirectly combined through another object.

Analytes

Examples that can use analytes involved in the present invention include some haptenic substances, including drugs (e.g., drugs of abuse). "Drugs of abuse" (DOA) refers to the use of drugs for non-medical purposes (usually playing a role in paralyzing nerves). Abuse of these drugs will lead to physical and mental damage to cause dependence, addiction and/or death. Examples of drugs of abuse include cocaine; amphetamine AMP (e.g., Black Beauty, white amphetamine tablets, dextroamphetamine, dexedrine tablets, Beans); methamphetamine MET (crank, methamphetamine, crystal, speed); barbiturate BAR (such as Valium□, Roche Pharmaceuticals, Nutley, New Jersey); sedatives (i.e., sleep aid drugs); lysergic acid diethylamide (LSD); inhibitors (downers, goofballs, barbs, blue devils, yellow jackets, methaqualone); tricyclic antidepressants (TCA, i.e., imipramine, amitriptyline, and doxepin); methylene dioxymetham-phetamine MDMA; phencyclidine (PCP); tetrahydrocannabinol (THC, pot, dope, hash, weed, etc.) ; opiates (i.e., morphine MOP or opium, cocaine COC; heroin, oxycodone); anxiolytics and sedative-hypnotics, and the anxiolytics are a class of drugs mainly used for reducing anxiety, tension and fear and stabilizing mood and having both hypnotic and sedative effects, including benzodiazepines BZO, atypical BZs, fusion diazonium NB23Cs, benzodiazepines, ligands for BZ receptors, and open-ring BZs, diphenylmethane derivatives, piperazine carboxylates, piperidine carboxylates, quinazolinones, thiazine and thiazole derivatives, other heterocycles, imidazole-type sedatives/analgesics (such as oxycodone OXY, methadone MTD), propylene glycol derivatives—carbamates, aliphatic compounds, anthracene derivatives, etc. A detection device using the present invention may also be used for detection of drugs that belong to medical purposes but are prone to overdose, such as tricyclic antidepressants (imipramine or analogues) and acetaminophen. These drugs will be decomposed into different small molecular substances after being absorbed by the human body. These small molecular substances exist in blood, urine, saliva, sweat and other body fluids or in some body fluids.

For example, analytes detected with the present invention include, but are not limited to, creatinine, bilirubin, nitrite, proteins (non-specific), hormones (e.g., human chorionic gonadotropin, progesterone hormone, follicle stimulating hormone, etc.), blood, leukocytes, sugars, heavy metals or toxins, bacterial substances (such as proteins or carbohydrates against specific bacteria, e.g., *Escherichia coli* 0157: H7, *Staphylococcus, Salmonella, Clostridium, Campylobacter, L. monocytogenes, Vibrios,* or *Bacillus cereus*) and substances associated with physiological characteristics in urine samples, such as pH and proportion. Any other clinical urine chemical analysis can use a lateral flow detection form to cooperate with the device of the present invention for detection.

Test Elements

So-called "test elements" here refer to elements that can detect whether samples or specimens contain interested analytes. This detection is based on whatever technical principles, such as immunology, chemistry, electricity, optics, molecules, nucleic acids, physics, etc. The test elements may be selected from a lateral flow test strip, which can detect a variety of analytes. Of course, other suitable test elements may also be applied in the present invention.

Various test elements may be combined to be applied in the present invention. One form is test paper or lateral flow test paper. Test paper for analysis of analytes (such as drugs or metabolites indicative of medical conditions) in a sample may be in various forms, such as forms of immunoassay or chemical analysis. The test paper may use a non-competitive or competitive analysis mode. The test paper generally includes a water absorption material with a sample adding area, a reagent area and a test area. A fluid or liquid sample is added to the sample adding area and flows to the reagent area by capillary action. In the reagent area, the sample binds to a reagent if the analytes are present. The sample then continues to flow to the test area. For other reagents, if molecules that specifically bind to the analytes are immobilized in the test area, these reagents react with the analytes (if present) in the sample and bind the analytes in this area, or bind to a certain reagent in the reagent area. A label used for displaying a detection signal is present in the reagent area or a separate labeling area.

A typical non-competitive analysis mode refers to that a signal will be generated if the sample contains the analytes, and no signal will be generated if the sample does not contain the analytes. In a competition method, a signal will be generated if the analytes are not present in the sample, and no signal will be generated if the analytes are present.

The test elements may be test paper, which may be selected from materials that absorb or do not absorb water. The test paper may include a variety of materials for liquid sample transfer. One of the materials of the test paper can cover another material, for example, filter paper covers a nitrocellulose membrane. One of the areas of the test paper may be selected from one or more materials, while the other area is selected from other different one or more materials. The test paper can be adhered to certain support or hard surface to improve the strength of holding the test paper.

The analytes are detected by a signal generating system, for example, by using one or more enzymes that specifically react with the analytes, and by using the method of immobilizing the specific binding substance on the detection test paper as described above, one or more combinations of the signal generating system are immobilized on the analyte test area of the test paper. A substance generating signals may be in the sample adding area, the reagent area, or the test area, or on the entire test paper, and the substance may fill on one or more materials of the test paper. A signal-substance-containing solution is added to the surface of the test paper or one or more materials of the test paper are immersed in the signal-substance-containing solution. The test paper to which the signal-substance-containing solution is added is dried.

The respective areas of the test paper may be arranged in the following ways: a sample adding area, a reagent area, a test area, a control area, an area for determination of whether a sample is adulterated or not, and a liquid sample absorption area. The control area is located behind the test area. All the areas may be arranged on a strip of test paper using only one material. Different materials may also be used for different areas. The respective areas may be in direct contact with the liquid sample, or different areas are arranged according to the flow direction of the liquid sample, and a tail end of each area is connected and overlapped with a front end of another area. The materials used may be materials with a better water absorption property, such as filter paper, glass fiber or nitrocellulose membranes. The test paper may also use other forms.

Generally, a commonly used reagent strip is a nitrocellulose membrane reagent strip, that is, a detection area includes a nitrocellulose membrane (NC), and specific binding molecules are immobilized on the nitrocellulose membrane to display detection results; it may also be a cellulose acetate membrane or a nylon membrane, etc. For example, reagent strips or devices containing reagent strips are described by the following patents: U.S. Pat. Nos. 4,857, 453; 5,073,484; 5,119,831; 5,185,127; 5,275,785; 5,416, 000; 5,504,013; 5,602,040; 5,622,871; 5,654,162; 5,656, 503; 5,686,315; 5,766,961; 5,770,460; 5,916,815; 5,976, 895; 6,248,598; 6,140,136; 6,187,269; 6,187,598; 6,228, 660; 6,235,241; 6,306,642; 6,352,862; 6,372,515; 6,379, 620; and 6,403,383. The test strips and similar devices with test strips disclosed in the above patent documents can all be applied to the test elements or detection devices of the present invention to detect the analytes, such as the detection of the analytes in the sample.

Detection reagent strips applied to the present invention may be commonly called lateral flow test strips. The specific structures and detection principles of these detection reagent strips are technologies well known to those of ordinary skill in the art in the prior art. A common detection reagent strip 30 (FIG. 1) includes a sample collection area or a sample adding area 70, a labeling area (40), a detection area 20 and a water absorption area 30. The sample collection area includes a sample receiving pad. The labeling area includes a labeling pad. The water absorption area may include a water absorption pad. The detection area includes necessary chemical substances, such as immunological reagents or enzymatic chemical reagents, which can detect whether an analyte is contained or not. Generally, a commonly used detection reagent strip is a nitrocellulose membrane reagent strip, that is, a detection area 202 includes a nitrocellulose membrane, and specific binding molecules are immobilized on the nitrocellulose membrane to display a detection result area; it may also be a cellulose acetate membrane or a nylon membrane, etc. Of course, a detection result control area 203 may also be included downstream of the detection area 202. Usually, a control area and the detection area appear in a form of horizontal lines, which are detection lines or control lines. Such detection reagent strips are traditional reagent strips, and of course, they may also be other types of reagent strips that utilize capillary action for detection. In addition, general detection reagent strips have dry chemical reagent components, such as immobilized antibodies or other reagents. When they encounter a liquid, the liquid flows along the reagent strips with capillary action, and with the flow, the dry reagent components are dissolved in the liquid, thus proceeding to the next area, the dry reagents in this area are processed, to perform necessary detection. Liquid flow proceeds mainly through capillary action. Here, all of them can be applied to the detection device of the present invention, or arranged in a detection chamber to be in contact with a liquid sample, or used for detecting the presence or the absence of an analyte in the liquid sample entering the detection chamber or the quantity of the presence thereof.

In addition to that the above test strips or the lateral flow test strips themselves are used for being in contact with the liquid sample to test whether the liquid sample contains the analyte, the test element of the present invention itself can be used as a detection device to detect the analyte in the sample, so the detection device itself is equivalent to the test element here. For example, after a fluid sample is mixed with a treatment liquid, the test element is directly used for detection. As will be described in detail below, the test element may be used alone for detection while it is described that a receiving device is used for processing the fluid sample.

In some manners, the labeling area of the present invention includes a plurality of labeling area bodies 40 overlapped. "a plurality of" in the present invention means more than one or one or more areas. For example, there are 3 to 8 or more labeling area bodies. For example, as shown in FIG. 1, the plurality of labeling area bodies 40 are 4 labeling area bodies.

In some manners, each labeling area body consists of one labeling pad, i.e., one labeling pad is one labeling area body. Overlapping with each other in the present invention means that the plurality of labeling area bodies are arranged on the test paper in order in a longitudinal direction of the test strip, for example, as shown in FIG. 1. This arrangement is not end-to-end connection, but end-to-end overlapping with each other. The so-called "overlapping" means that the two marking pads are overlapped and combined with each other, and have interlaced places. For example, as shown in FIG. 1, reference signs 41 and 42 are two different areas of one marking pad 46, namely an area 41 treated with labeling substances and an area 42 not containing the labeling substances. In this way, there are three other labeling pads 43, 44 and 45 with the same areas, each labeling pad including a labeling-substance-containing area and a labeling-substance-free area. Here, a first labeling pad is located downstream of a sample pad 70, a second labeling pad 43 is located downstream of the first labeling pad, a third labeling pad 44 is located downstream of the second labeling pad, and a fourth labeling pad is located downstream of the third labeling pad. In one manner, an overlapping mode is as follows. A white blank area 42 of the first labeling pad is located above a labeling colored area of the second labeling pad 43, and a white area of a second marking substance is located above a labeling substance area of the third labeling pad, which overlap with each other. In this pattern, the 4 labeling pads are overlapped with each other end to end. Of course, when connected with an NC film, a white labeling-substance-free area of a fourth labeling pad 45 overlaps with one end 202 of the NC film, and there is a mutual overlapping area 46.

In some manners, generally, one labeling pad is 6 to 8 mm in length, a labeling-substance-free area is 2 to 3 mm in length, and a labeling-substance-containing area is 3 to 5 mm in length, for example, a labeling-substance-free area is 3 mm in length, a labeling-substance-containing area is 5 mm in length, and a length of an area overlapped with the second labeling pad 43 is 1 mm. At least, not the entire white labeling-substance-free area is overlapped with the labeling-substance-containing area of the second labeling pad 43 to cover the second labeling pad 43, but part of a labeling-substance-free area of the first labeling pad. According to the above principles, a plurality of labeling pads may be overlapped and connected with each other. In some manners, the labeling substances herein include colored particles and antibodies specifically binding analytes or coupled with antigens. These labeling substances can be moved by a liquid sample and flow to the downstream NC film, for example, they pass through the detection area 202 and the control area 203 of the NC film, and finally are absorbed by an absorption pad 30.

In some manners, an area of the labeling substances is covered with a layer of strap 80, and the "strap" here means being similar to a fixing strap, one end thereof is connected to the sample pad 70 and the other end thereof is connected to the NC film, and it covers the plurality of labeling pads, so that the labeling pads are overlapped with each other more closely, thereby avoiding the change of mutual positions of the sample pads. The strap has two faces, one face is a face facing the labeling pad, and the other is a face that faces outward. The face of the strap 80 facing the labeling pad has a glue layer, which is adhered to each labeling pad, so that the overlapped areas of the labeling pads are more closely adhered, one end covers part of the sample pads, and the other end covers the NC film, so that a white labeling-pad-free area of the fourth labeling pad is more tightly adhered onto of one end 201 of the NC film.

In one manner, the sample pad 70 has an area partially covering the entire first labeling pad 46 and also covering part of a labeling substance area of part of the second labeling pad 43. In some manners, the strap is also covered with strips 50, basically 4 strips, which are adhered to the strap, so that the 4 strips basically cover an area where the two labeling pads are overlapped, so that the multiple labeling pads are more closely matched, and form a complete test strip together with the NC film and the sample pads.

In some manners, the labeling substances in the labeling areas of the plurality of labeling pads are the same, and the labeling substances include colored particles and coupled antibodies specifically binding to analytes in a sample. For example, the antibodies may be antibodies to small drug molecules. When detection by a competition method, antigens of the small drug moleculea are immobilized on the detection area. For example, when THC is detected, the labeling areas are all coated with antibodies specifically binding to THC in a sample. The antibodies are coupled to labeling substances of gold particles or latex particles. These gold particles or latex particles may be millimeter or nanoscale particles in diameter. Antigens corresponding to THC are immobilized on the detection area, for example, THC molecules are connected to BSA to become antigens. In this way, when the sample contains the THC, the THC molecules in the sample are connected to the antibodies on the labeling pads, and when they flow to a detection line, the THC antigens immobilized on the detection line compete with the small THC molecules in the sample for binding to the antibodies coupled with labeling particles. It is also a technical content known in the art, and will not be described again.

Traditional test strips generally have only one labeling pad. The entire labeling pad is sprayed with a labeling substance, and does not include a white labeling-substance-free area. However, each labeling substance pad of the present invention includes two areas, namely a labeling-substance-containing area and a labeling-substance-containing blank area. In addition, there is only one traditional labeling pad. In addition, the length thereof may be longer. However, there are multiple labeling pads in the present invention, and a blank area of a first labeling pad covers a labeling substance area of a second labeling pad, so that the multiple labeling substances are connected and cover in this way. In this way, the sensitivity of detection and the degree of distinguishing of detection can be improved, and especially for the small drug molecule THC, the sensitivity and degree of distinguishing of detection can be improved. In addition, it can obviously have a gradient, which is easier to identify, and especially when an analyte in a sample is near a detection threshold value, it is hoped that it can be prepared to distinguish between negative and positive. Therefore, when a threshold value is selected, distinguishing properties of a test strip are detected at a −50% cut off value and a +50% cut off threshold value, if the two have different threshold value levels, and if color lines are more clearly distinguished, it means that in actual detection, the lines are clearly distinguished, and positive or negative samples can be easily distinguished. The distinguishing properties here are that the greater the difference in color grades, the more obvious the distinguishing. A negative result here does not mean that the sample does not contain THC, but that it is considered a negative result if the content is lower than a certain threshold value. After all, it is a test for detection of drug abuse. If drug abuse is reached, the content of the analyte in the sample is relatively high. When there is no abuse but normal use, the content in the sample is very low, but it does not mean that it does not contain the analyte. Therefore, the threshold value is a variable value, and it is constant for a period of time, and may also be stipulated according to actual situations of different countries.

For example, when a detection threshold value of THC is 50 ng/ml, if detection is performed at a −50% cut off quality control product (25 ng/ml) and a +50% cut off quality control product (saliva) (75 ng/ml), and if the difference between the lines in colors is large, they are easy to distinguish in actual detection without causing false positive or false negative results. THC is a special small drug molecule. Generally, the content of THC in samples, such as urine or saliva, is small. A current detection threshold value is set to 50 ng/ml. When the content thereof is higher than this threshold value in the sample, it is positive, and when the content thereof is lower than this threshold value, it is negative. When the competition method is used, the positive result shows no line, while the negative result shows a line. The darker the color of the line, the lower the content in the sample or the absence.

DETAILED DESCRIPTION OF THE EMBODIMENTS

The present invention will be further described below in combination with accompanying drawings and embodiments. It should be noted that the embodiments are only a detailed description of the present invention, and cannot be used to limit the protection scope of the present invention. All features disclosed in the embodiments of the present invention, or all disclosed methods or steps in a process, except for mutually exclusive features and/or steps, can be combined in any way within the protection scope of the present invention. The technologies not involved in the present invention can be implemented by the prior art.

Embodiment 1 Test Strip

Figure 2:
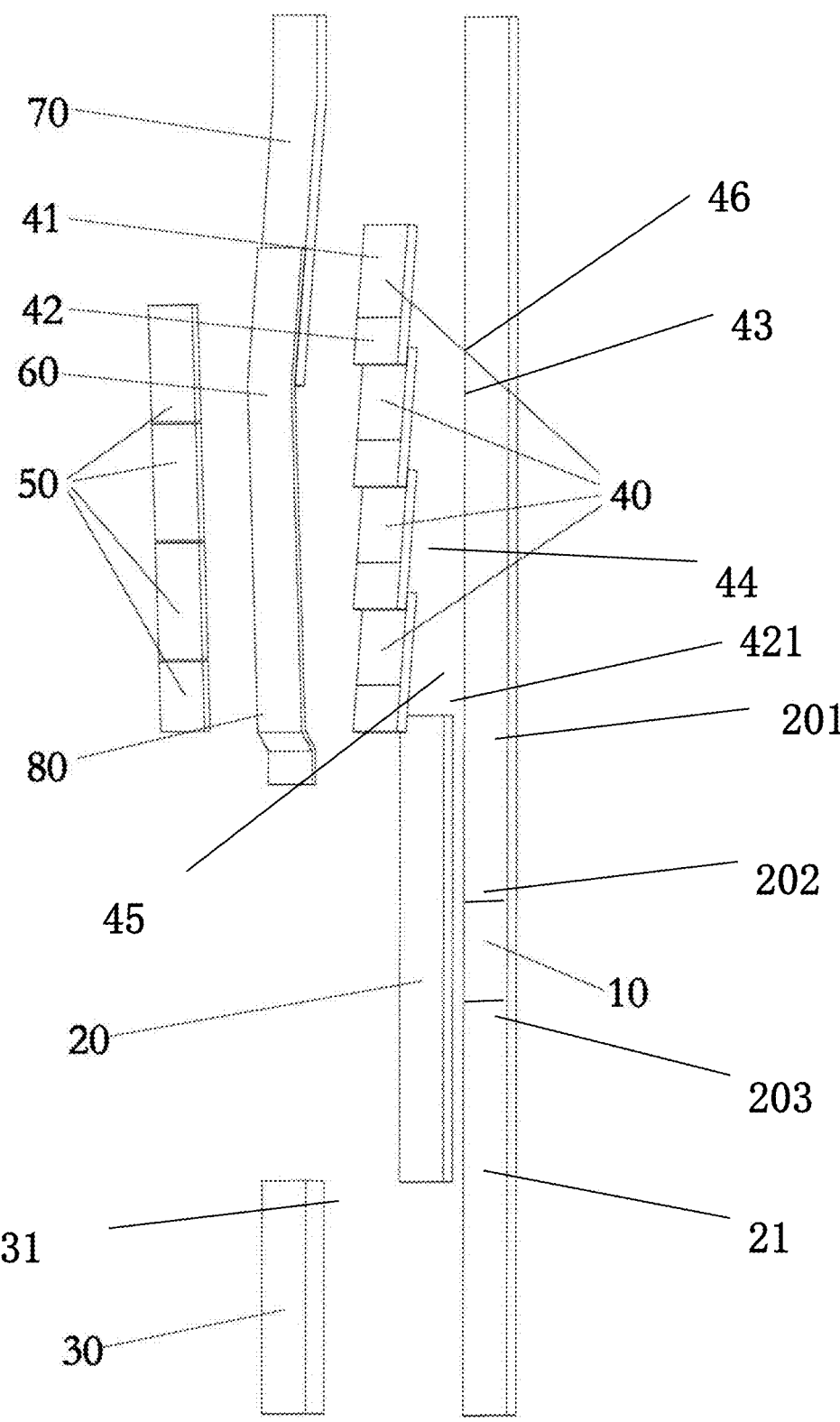
FIG. 2 is an exploded view of the test strip of the present invention.

As shown in FIGS. 1 to 2, a test strip includes a test strip main body 10. The test strip main body 10 is made of a PVC material and serves as a support pad. The support pad is sequentially provided with a sample section 70, a plurality of colloidal gold pads 40, an NC film 20 and a water absorption end 30. A sample pad is used for applying a liquid sample. The colloidal gold pads 40 are of 4 layers or are 4 colloidal pads, which can also be referred to as labeling pads here. Each colloidal gold pad 40 is made by smearing (or mechanically spraying) colloidal gold on non-woven fabric (or glass fiber), and is divided into a colored part 41 and a white edge part 42, the colored part 41 being a smear area of the colloidal gold, and the white edge part 42 being an area where the colloidal gold is not smeared.

The colored area here is generally an area sprayed or coated with a labeling substance. The labeling substance may be colored particles, and the colored particles may be latex or gold particles. A specific method for processing the colored area is the prior art disclosed, and will not be described in detail here. In some manners, the colored area is approximately 2, 3, or 4 times, etc. the size of the white area.

The respective colloidal gold pads 40 are overlapped in a straight line; and the white edge part 42 of an adjacent colloidal gold pad is overlapped on the colored part 41 of another colloidal gold pad. A length of the white edge part 42 is generally 2 to 6 mm, and in this specific embodiment, the length thereof is 2 mm, and a length of the colored part of the colloidal gold is 6 mm. A length of an overlapping area of the white edge part 42 of one of the colloidal gold pads and the colored part 41 of the adjacent colloidal gold pad is not more than 6 mm, and the length thereof in this embodiment is 4 mm. If further, the colored part 41 of the colloidal gold pads is overlapped with the colored part 41 of the adjacent colloidal gold pad, and an overlapping length thereof is not more than 6 mm, and a preferred overlapping length is not more than 5 mm, for example, it may be 1 mm, 2 mm, 3 mm or 4 mm. The NC film 20 is a nitrocellulose membrane, an upper end thereof is in contact with a white edge part 42 of a nearest colloidal gold pad 40, and a lower end thereof is in contact with the water absorption end 30. A specific contact mode is that there are 4 labeling pads in this embodiment, and each labeling pad includes an area 41 sprayed with a labeling substance and an area 42 not sprayed with a labeling substance. For example, there are first, second, third and fourth labeling pads in sequence from upstream to downstream, a white area of the first labeling pad is overlapped on a colored area of the second labeling pad, and an overlapping length thereof is 2 mm, an overlapping mode of the second and third labeling pads is the same as that of the first and second labeling pads, and an overlapping mode of the third and fourth labeling pads is the same. On a last labeling pad, a white area 401 thereof is overlapped on one end 201 of a detection area pad. A detection area in this embodiment is the NC film, and there is a detection area 202 and a detection result control area 201 on the film. One end 31 of an absorption pad 30 is overlapped on the other end 21 of the NC film.

The above test strip includes a strap 80. The strap 80 may have an adhesive property on one face, part of one end of the strap 80 covers the sample section 70, and the other end thereof is connected to one end of the NC film. The sample section 70 is selected from a non-woven fabric or glass fiber material, and is adhered to the test strip main body 10 through glue to serve as a sample adding area. The strap 80 has an adhesive sticker section 60 which is sticky and sticks to the NC film. The strap 80 completely covers the 4 colloidal gold pads 40, so that the respective colloidal gold pads 40 are overlapped more closely to prevent a change in mutual positions. The strap 80 is covered with 4 strips 50. The strips 50 are PVC (polyvinyl chloride) strips or PS (polystyrene) strips, and are adhered to each other and play a further fixing role, enabling the colloidal gold pads 40 to be overlapped more tightly.

In addition, the water absorption end 30 of the above test strip is made of a water-absorbing material, which may be water-absorbing filter paper, water-absorbing sponge, or the like. An upper end of the water absorption end 30 is in contact with the NC film, and a lower end thereof is flush with a lower end of the test strip main body 10.

The above upper and lower ends are based on a length direction of the test strip main body 10. A direction of the test strip main body 10 close to the water absorption end 30 is a downstream direction, and a direction close to the sample section 70 is an upstream direction. A liquid generally flows from upstream to downstream. The NC film is downstream of the labeling pads, which are generally downstream of the sample pad.

Embodiment 2 Sensitivity Comparison Experiment (1) THC (tetrahydrocannabinol) test products of a competition method are selected, and assembled according to the prior art to make a THC test strip containing 1 layer of colloidal gold pad (before improvement) and a THC test strip containing 5 layers of colloidal gold pads described in Embodiment 1 (after improvement). A material of an NC film and a material of a sample pad are the same, and reagents for treatment are also the same. The only difference is in labeling pads, labeling substances of the same cost are sprayed on one labeling pad before improvement, while after the improvement, they are sprayed evenly on 5 labeling pads respectively.

Figure 3:
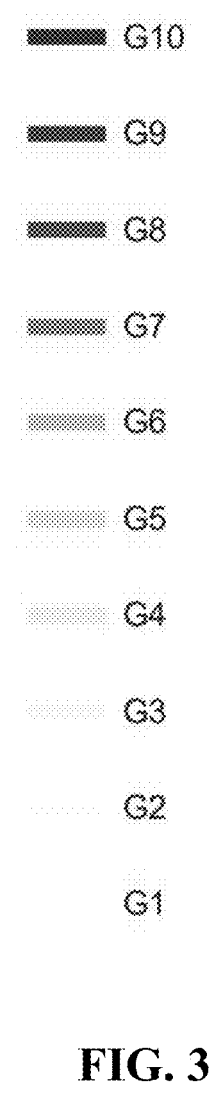

The test strips before and after improvement are used for respectively testing negative (NEG) (without THC), a −50% cut off quality control product (25 ng/ml), and a +50% cut off quality control product (saliva) (75 ng/ml), wherein a cut off value of THC is 50 ng/ml, as well as 10 clinical human specimens (saliva samples, which are determined to be negative samples by chromatography), to observe signal intensity. The signal intensity is compared with a color card (FIG. 3), to record experimental results. The experimental results are shown in Table 1 below. The color card is recorded as G1 to G10 according to colors from light to dark. The larger the G value, the stronger the signal, and the lower the amount of THC; the smaller the G value, the weaker the signal, and the higher the amount of THC.

TABLE 1

Comparison table of test results of THC
test strips before and after improvement

| Sample names | | Experimental results | |
| --- | --- | --- | --- |
| | | Before improvement | After improvement |
| Quality control products | NEG (negative) | G5 | G7 |
| | | G4.5 | G6 |
| | −50% cutoff | G4 | G3 |
| | +50% cutoff | | |
| Clinical specimens | 1 | G5 | G8.5 |
| | 2 | G5 | G8.5 |
| | 3 | G6 | G8.5 |
| | 4 | G7 | G8 |
| | 5 | G5 | G8.5 |
| | 6 | G6.5 | G8.5 |
| | 7 | G5 | G8 |
| | 8 | G6 | G8.5 |
| | 9 | G6.5 | G8.5 |
| | 10 | G6 | G9 |

From results in Table 1, it can be seen that signals measured by a THC test strip with 5 layers of colloidal gold pads (after improvement) are stronger, and the color of the -50% cut off quality control product is G6 and the color of the +50% cut off quality control product is G3, the range of detection results is wider, and there is a difference of 3 color grades; it is shown that the THC test strip with 4 layers of colloidal gold pads (after improvement) has higher sensitivity and specificity, making detection results more reliable, and may also be used for detection of lower-concentration samples. It is indicated that for 1 labeling pad included, the color of the corresponding 50% cut off quality control product is G4.5 and the color of the +50% cut off quality control product is G4, with a difference of 0.5 color grade. In this way, when it is near a detection threshold value, it is difficult to directly distinguish between negative and positive, which will cause false positives or false negatives.

(2) HCG (human chorionic gonadotropin) test products of a sandwich method are selected, and assembled according to the prior art to make an HCG test strip containing 1 layer of colloidal gold pad (before improvement) and an HCG test strip containing 4 layers of colloidal gold pads described in Embodiment 1 (after improvement). The test strips before and after improvement are used for respectively testing a 10 miU/ML quality control product, a 25 miU/ML quality control product, a 100 miU/ML quality control product, a 500 miU/ML quality control product as well as 10 clinical human negative specimens and 10 pregnancy specimens, to observe signal intensity. The signal intensity is compared with a color card to record experimental results. The experimental results are shown in Table 2 below. The color card is recorded as G1 to G10 according to colors from light to dark. The larger the G value, the stronger the signal, and the higher the amount of HCG; the smaller the G value, the weaker the signal, and the lower the amount of HCG.

TABLE 2

Comparison table of test results of HCG
test strips before and after improvement

| | | Experimental results | |
| | Sample names | Before improvement | After improvement |
|---|---|---|---|
| Quality control products | 10 miU/ML | G3 | G4 |
| | 25 miU/ML | G4 | G5 |
| | 100 miU/ML | G6 | G7 |
| | 500 miU/ML | G8 | G9 |
| Clinical negative samples | 1 | G1 | G1 |
| | 2 | G1 | G1 |
| | 3 | G2 | G1 |
| | 4 | G1 | G1 |
| | 5 | G1 | G1 |
| | 6 | G1 | G1 |
| | 7 | G2 | G1 |
| | 8 | G1 | G1 |
| | 9 | G1 | G1 |
| | 10 | G2 | G1 |
| Clinical pregnancy (positive) samples | 1 | G9 | G9 |
| | 2 | G9 | G9 |
| | 3 | G8 | G9 |
| | 4 | G10 | G10 |
| | 5 | G7 | G7 |
| | 6 | G8 | G8 |
| | 7 | G8.5 | G9 |
| | 8 | G8 | G9 |
| | 9 | G9 | G9 |
| | 10 | G9 | G9 |

It can be seen from results in Table 2 that signals measured by the HCG test strip with 4 layers of colloidal gold pads (after improvement) are stronger, and signals of the clinical negative samples are lower, and signals of the positive quality control products are stronger. The results show that compared with the HCG test strip with 1 layer of colloidal gold pad, the HCG test strip with 4 layers of colloidal gold pads (after improvement) has higher sensitivity and specificity, making detection results more reliable, and enabling to detect lower-concentration HCG samples.

All patents and publications mentioned in the specification of the present invention indicate that these are disclosed techniques in the art, and the present invention can use them. All patents and publications cited herein are also listed in references as each publication is specifically and individually referred and cited. The present invention described herein may be implemented in the absence of any element or elements, limitation or limitations, no such limitation specifically stated herein. For example, the terms "comprising", "essentially consisting of . . . " and "consisting of . . . " in each embodiment herein may be replaced by either of the remaining two terms. So-called "one" here only means "one", and it does not exclude that only one is included, and it may also mean that two or more are included. The terms and expressions used herein are description modes, and are not limited by them. There is no any intention here to indicate that these terms and interpretations described in this specification exclude any equivalent features, but it can be known that any suitable changes or amendments may be made within the scopes of the present invention and the claims. It can be understood that the embodiments described in the present invention are all preferred embodiments and features, and any person of ordinary skill in the art can make some amendments and changes according to the essence of the description of the present invention, and these amendments and changes are also considered to belong to the scope of the present invention and the scopes defined by the independent and dependent claims.

The invention claimed is:

1. A test strip for detecting an analyte in a sample, comprising a test strip main body, wherein the test strip main body is sequentially provided with a sample pad, a labeling pad, a nitrocellulose (NC) film with a detection area, and a water absorption area pad; and the labeling pad comprises a plurality of labeling pad bodies overlapped end to end with each other;

wherein labeling substances on the labeling pad bodies are the same labeling substance;

wherein the labeling substances in a labeling area comprise antibodies specifically binding to the analyte in the sample and colored particles coupled with the antibodies;

wherein the labeling pad bodies comprise colored areas sprayed with the labeling substances and white areas not containing the labeling substances;

wherein the antibodies on the labeling pad bodies are antibodies specifically binding to tetrahydrocannabinol (THC), and the detection area on the NC film comprises THC antigens;

wherein the labeling pad bodies are five labeling pad bodies overlapped end to end.

2. The test strip according to claim 1, wherein a length of the white areas is 2 to 8 mm.

3. The test strip according to claim 1, wherein a length of the colored areas is 2 to 8 mm.

4. The test strip according to claim 1, wherein the plurality of labeling pad bodies are overlapped end to end in a straight line; and a white area part of one of a plurality of colloidal gold pads is overlapped on an upper side of a colored part of another adjacent colloidal gold pad.

5. The test strip according to claim 4, wherein an overlapping length of a white part of one of the plurality of labeling pad bodies and a colored part of another one of the plurality of labeling pad bodies is not more than 6 mm.

6. The test strip according to claim 5, wherein an overlapping length of a white part of one of the plurality of labeling pad bodies and a colored part of another one of the plurality of labeling pad bodies is not more than 5 mm.

7. The test strip according to claim 6, wherein an overlapping length of a white part of one of the plurality of labeling pad bodies and a colored part of another one of the plurality of labeling pad bodies is not more than 4 mm.

8. The test strip according to claim 6, wherein the labeling pad bodies are arranged in sequence from upstream to downstream.

9. The test strip according to claim 6, wherein the labeling substances comprise gold particles or latex particles.

10. The test strip according to claim 1, wherein the test strip comprises a strap for covering the labeling pad bodies, one end of the strap covering the sample pad, and the other end thereof being connected to NC.

11. The test strip according to claim 10, wherein a material of the sample pad is non-woven fabric or glass fiber.

12. The test strip according to claim 10, wherein the strap is provided with strips, so that the labeling pad bodies can be overlapped tightly; the number of the strips is greater than or equal to 2; and the strips comprise polyvinyl chloride (PVC) strips or polystyrene (PS) strips.

13. A test strip for detecting an analyte in a sample, comprising a test strip main body, wherein the test strip main body is sequentially provided with a sample pad, a labeling pad, an NC film with a detection area, and a water absorption area pad; and the labeling pad comprises a plurality of labeling pad bodies overlapped end to end with each other;

wherein labeling substances on the labeling pad bodies are the same labeling substance;

wherein the labeling substances in a labeling area comprise antibodies specifically binding to the analyte in the sample and colored particles coupled with the antibodies;

wherein the labeling pad bodies comprise colored areas sprayed with the labeling substances and white areas not containing the labeling substances;

wherein the antibodies on the labeling pad bodies are first antibodies specifically binding to human chorionic gonadotropin (HCG), and the detection area on the NC film comprises second antibodies specifically binding to the HCG;

wherein the labeling pad bodies are four labeling pad bodies overlapped end to end.

\*    \*    \*    \*    \*